United States Patent
Faus et al.

(10) Patent No.: US 6,667,802 B2
(45) Date of Patent: Dec. 23, 2003

(54) SYSTEM AND METHOD FOR SELF-REFERENCING CALIBRATION

(75) Inventors: Robert J. Faus, Longmont, CO (US); Brian Curtiss, Boulder, CO (US); Daniel A. Powell, Boulder, CO (US)

(73) Assignee: Analytical Spectral Devices, Inc., Boulder, CO (US)

(*) Notice: Subject to any disclaimer, the term of this patent is extended or adjusted under 35 U.S.C. 154(b) by 116 days.

(21) Appl. No.: 10/068,623

(22) Filed: Feb. 5, 2002

(65) Prior Publication Data

US 2002/0109839 A1 Aug. 15, 2002

Related U.S. Application Data

(60) Provisional application No. 60/268,483, filed on Feb. 12, 2001.

(51) Int. Cl.[7] .................................................. G01J 3/28
(52) U.S. Cl. .................. 356/300; 356/326; 250/339.07; 250/339.11
(58) Field of Search ................................ 356/300, 326, 356/328, 425; 250/339.07, 339.11; 209/577

(56) References Cited

U.S. PATENT DOCUMENTS

| | | |
|---|---|---|
| 4,143,770 A | 3/1979 | Grimmell et al. |
| 4,893,253 A | 1/1990 | Lodder |
| 5,504,332 A | 4/1996 | Richmond et al. |
| 5,522,512 A | 6/1996 | Archer et al. |
| 5,679,954 A | 10/1997 | Soloman |
| 5,750,996 A | 5/1998 | Drennen, III et al. |
| 5,900,634 A | 5/1999 | Soloman |

FOREIGN PATENT DOCUMENTS

| | | |
|---|---|---|
| EP | 0 887 638 A1 | 12/1998 |
| EP | 0 959 342 A2 | 11/1999 |
| EP | 0 959 342 A3 | 1/2000 |
| WO | WO 96/32631 A1 | 10/1996 |
| WO | WO 01/03646 A3 | 1/2001 |
| WO | WO 01/03646 A2 | 1/2001 |

OTHER PUBLICATIONS

MacDonald B. F., et al.: "Some Applications of Near–Infrared Reflectance Analysis in the harmaceutical Industry;" Journal of Pharmaceutical and Biomedical Analysis; vol. 11, No. 11–12, 1993, pp. 1077–1085, XP001098341; ISSN: 0731–7085; p. 1079, col. 1, Paragraph 3; p. 1080, col. 1, Paragraph 1.
Aldridge P. K., et al.: "Identification of Tablet Formulations Inside Blister Packages by Near–Infrared Spectroscopy;" Applied Spectroscopy; vol. 48, No. 10, 1994, pp. 1272–1276; XP001098336; Whole Document.
Blanco, M., et al.: "Identification and Quantitation Assays for Intact Tablets of Two Related Pharmaceutical Preparations by Reflectance Near–Infrared Spectroscopy: Validation of the Procedure;" Journal of Pharmaceutical and Biomedical Analysis; vol. 22, No. 1, Feb. 2000, pp. 139–148, XP002212018; ISSN: 0731–7085; Whole Document.
Copy of the International Search Report for PCT Application Serial No. PCT/US02/03285, mailed on Sep. 24, 2002.
Copy of the International Search Report for PCT Application Serial No. PCT/US02/03287, mailed on Sep. 24, 2002.
Copy of the International Search Report for PCT Application Serial No. PCT/US02/03288, mailed on Sep. 24, 2002.
Copy of the International Search Report for PCT Application Serial No. PCT/US02/03286, mailed on Oct. 14, 2002.

*Primary Examiner*—F. L. Evans
(74) *Attorney, Agent, or Firm*—Cooley Godward LLP

(57) ABSTRACT

A method of calibrating a spectrographic inspection system, comprises providing a plurality of packages, each of the plurality of packages containing a group of items, wherein each of the groups of items has a known composition, measuring the reflectance value of each of the groups of items and thereby obtaining a reference reflectance value set, normalizing the reference reflectance value set and thereby creating a normalized reference reflectance value set, and storing the normalized reference reflectance value set.

22 Claims, 6 Drawing Sheets

SYSTEM AND METHOD FOR SELF-REFERENCING CALIBRATION

PRIORITY

The present application claims priority to U.S. provisional application No. 60/268,483 and titled NIR Screening of Materials to Be Packaged, filed on Feb. 12, 2001, which is hereby incorporated by reference.

RELATED APPLICATIONS

The present application is based on disclosure document No. 481228 deposited with the U.S. Patent and Trademark Office on Oct. 17, 2000. The present application is also related to U.S. patent application Ser. No. 10/023,302, filed on Dec. 20, 2001 and titled System and Method for Grouping Reflectance Data, U.S. patent application Ser. No. 10/023,395, filed on Dec. 20, 2001 and titled System and Method for Combining Reflectance Data and U.S. patent application Ser. No. 10/023,396, filed on Dec. 20, 2001 and titled System and Method for the Collection of Spectral Image Data. Each of the above applications are hereby incorporated by reference.

FIELD OF THE INVENTION

The present invention pertains to spectrographic and reflectance data analysis and more particularly to screening and identifying materials, such as pharmaceutical or food products, being packaged in an automated machine.

BACKGROUND OF THE INVENTION

Optical spectrometers allow the study of a large variety of samples over a wide range of wavelengths. Materials can be studied in the solid, liquid, or gas phase either in a pure form or in mixtures. Various designs allow the study of spectra as a function of temperature, pressure, and external magnetic fields.

Near-Infrared (NIR) spectroscopy is one of the most rapidly growing methodologies in product analysis and quality control. In particular, NIR is being increasingly used as an inspection method during the packaging process of pharmaceuticals or food products. More and more often, this technique is augmenting or even replacing previously used vision inspection systems. For example, an NIR inspection system can be used to inspect a pharmaceutical blister package (such as an oral contraceptive or allergy medication) for, among other things, physical aberrations, chemical composition, moisture content, and proper package arrangement.

Most notably, NIR spectrometry inspection systems can be used to evaluate the chemical composition of products during the packaging process. Particularly with solid dosage pharmaceutical products, a group or package of products may look identical in the visible portion of the spectrum but may have unique chemical signatures in the near-infrared range (e.g. the 800–2500 nm range). Variations in the chemical composition of a tablet or capsule are usually grounds for rejecting a package containing a tablet with such a discrepancy. In operation on a pharmaceutical blister packaging machine, a still uncovered blister pack containing tablets or capsules passes an inspection station where it is examined. Once the inspection device inspects the blister pack to ensure that the correct material is located in each of the tablet or capsule wells, the packaging machine seals the blister pack. Those packages that fail the inspection process are rejected at a subsequent station. Subject to regulatory requirements, the rejected tablets may also be recycled for further processing.

The use of vision systems as an inspection mechanism continues to become less desirable as the need for more in depth inspection procedures and near 100% inspection processes are desired. Of particular concern is that known vision systems are inherently incapable of performing a chemical analysis of the product being packaged. Rather, vision systems rely solely on a comparison of a visual snapshot of the package to a previously stored reference image. Known vision packaging inspection systems "look" at each individual package to see whether it has the correct number of doses in the pack. For example, vision systems look for missing or overfilled tablet wells. In some cases, physical discrepancies, cracks, or gouges on a tablet will also cause a vision system to reject the package. What may not be detected by a vision system is the situation where each of the products in a package appears to be similar and in conformance with a reference image but the formulation of one or more products within the package are incorrect, or the wrong product composition is inserted into the packaging. The limitations of these types of known visions systems become readily apparent when higher levels of inspection are required and when they are compared with the expanded capabilities of a spectrometer-based inspection system.

In order to calibrate known spectrometer inspection systems, it is necessary to normalize the spectrometer to a stable reference sample. Typically, a material having a near 100% reflectance is selected for the reference material. The raw spectrum of this reference sample is measured by the spectrometer in order to provide a reference for normalizing subsequent measurements. This is done by dividing the measured raw spectrum of target samples by the previously measured raw spectrum of the reference sample. The normalized spectrum of the target sample is then used in conjunction with the previously established baseline to evaluate whether a discrepancy exists in the samples actually subjected to examination or inspection.

This method, however, requires that the packaging or inspection system be loaded with a stable reference sample, typically one with near 100% reflectance at the beginning of each packaging run in addition to providing known samples for comparison purposes. The addition of another step to the inspection process introduces other sources of error into the system and adds to the overall inspection time and cost.

It is therefore desirable to have a spectrometer-based inspection system that does not require a stable reference sample to be loaded into the packaging equipment in addition to a calibration set. It is also desirable to have a spectrometer-based inspection system that minimizes the number of steps required to obtain a relative spectrographic measurement of a package of items and that allows for calibrations specific to particular material properties applicable to a range of material compositions.

SUMMARY OF THE INVENTION

In one aspect, a method of calibrating a spectrographic inspection system, comprises providing a plurality of packages, each of the plurality of packages containing a group of items, wherein each of the groups of items has a known composition, measuring the reflectance value of each of the groups of items and thereby obtaining a reference reflectance value set, normalizing the reference reflectance value set and thereby creating a normalized reference reflectance value set, and storing the normalized reference reflectance value set.

In another aspect, a method of analyzing a package of items comprises providing a first package containing a first group of items, wherein the first group of items has a known composition, measuring the reflectance value of the first group of items, thereby obtaining a reference reflectance value, normalizing the reference reflectance value and thereby creating a normalized reference reflectance value, storing the normalized reference reflectance value, providing a second package containing a second group of items, wherein the second group of items has an unknown composition, measuring the reflectance value of the second group of items to obtain a target reflectance value, normalizing the target reflectance value and thereby creating a normalized target reflectance value, comparing the normalized target reflectance value with the normalized reference reflectance value, and determining whether the normalized target reflectance value conforms with the normalized reference reflectance value.

In a further aspect An inspection system, comprises an inspection station adapted to obtain reflectance data corresponding to a first package and adapted to gather reflectance data corresponding to a second package, and a processor communicatively coupled with the inspection station and adapted to normalize the reflectance data obtained by the inspection station, thereby creating normalized reflectance data, wherein the processor is further adapted to compare the reflectance data corresponding to the first package with the normalized reflectance data corresponding to the second package.

As will become apparent to those skilled in the art, numerous other embodiments and aspects will become evident hereinafter from the following descriptions and claims.

BRIEF DESCRIPTION OF THE DRAWINGS

The drawings illustrate both the design and utility of the preferred embodiments of the present invention, wherein.

DETAILED DESCRIPTION

Figure 1:
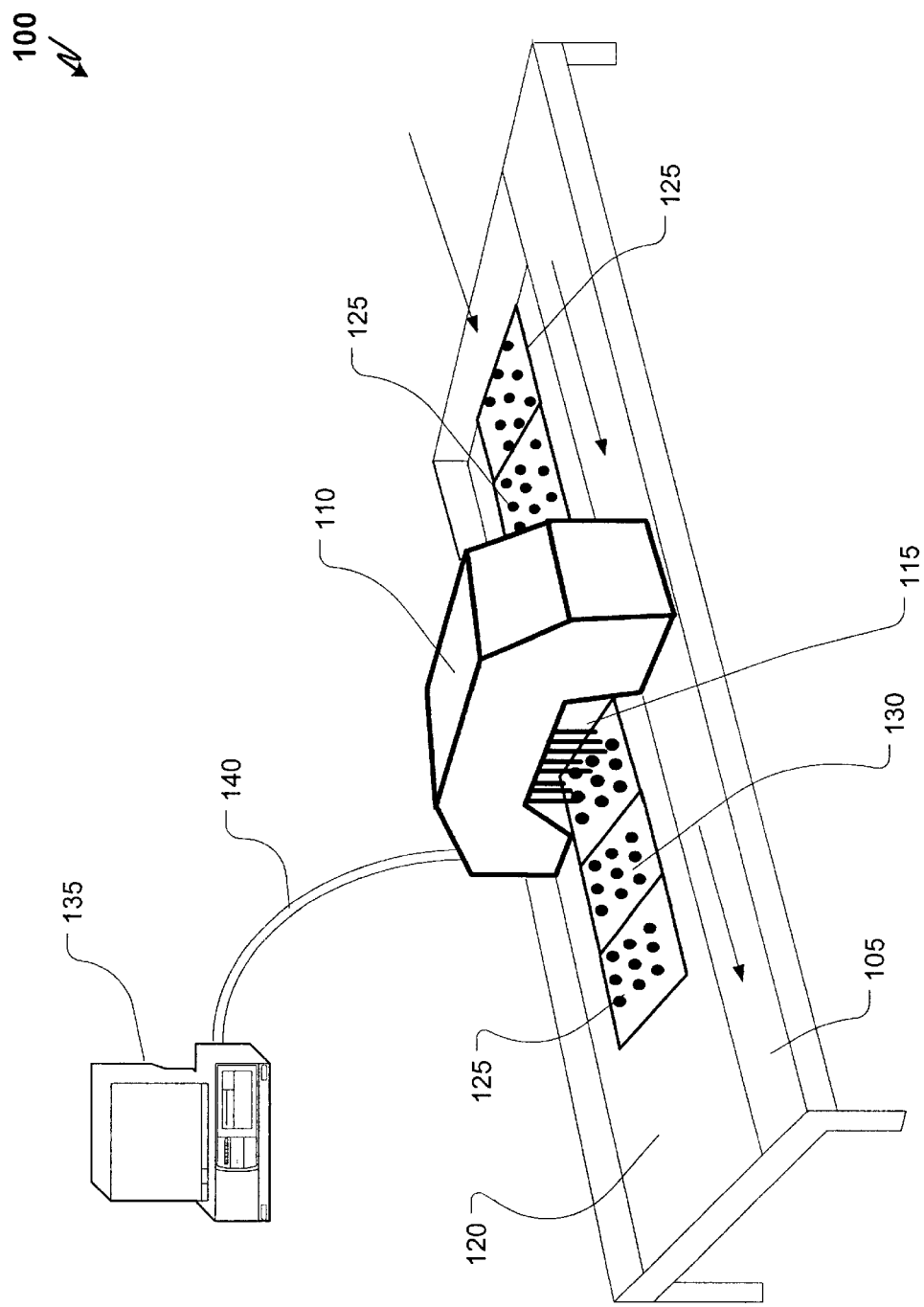
FIG. 1 is a general overview of an inspection system.

FIG. 1 depicts an inspection system 100. The inspection system 100 is generally arranged to allow the inspection of a product, for example tablets or capsules 130, that have been loaded into a package 125. As shown in FIG. 1, the packages 125 move along a conveyer 120 mounted within a filling unit 105. The filling unit 105 is preferably one component of a larger manufacturing and packaging system. As an example, such manufacturing and packaging systems are typically utilized in pharmaceutical and chemical manufacturing facilities, although similar systems are often utilized in other applications such as food processing and consumer product facilities. Aspects of the present invention can be applied to virtually any of these applications. For purposes of illustration only, the present invention will be described in conjunction with a pharmaceutical packaging system used to seal tablets or capsules in a blister-type package. Also shown in FIG. 1, and included as a component of the inspection system 100, is an inspection station 110 constructed in accordance with various aspects of the present invention.

The inspection station 110 bridges the conveyer 120 that carries the packages 125. The inspection station 110 includes an array of sample probes 115 extending downward from the inspection station 110 and substantially aligning with the passing packages 125. Generally, a light source (not shown) illuminates the packages 125 including the tablets 130 as they pass under the inspection station 110 and the sample probes 115. Light is reflected by the tablets 130 and the reflected light energy is gathered by one or more of the probes 115.

The reflected light energy gathered by each of the probes 115 preferably contains information about the properties of each of the tablets 130 that pass beneath the inspection station 110. Light energy gathered by the sample probes 115 is directed through fiber optic cables, to a spectrometer that is preferably housed within the inspection station 110 (not shown). The collected light energy is analyzed by the spectrometer according to predetermined criteria. The information generated by the spectrometer is then forwarded via a data cable 140 to a computer 135 for display, storage, or further analysis. The computer 135 may be preloaded with processing information pertaining to the specific packaging or inspection operation being conducted. The information gathered about the tablets 130 contained in each package 125 may then be used to determine whether the specific tablets being inspected conform with a predetermined quality criteria.

By gathering spectrographic data about each of the tablets 130, a determination can be made as to whether the packages have been properly filled or contain the proper product. Spectrographic analysis also allows other determinations to be made that are not available with known vision-based systems, such as proper pharmacological composition, water content, and other chemical and physical properties. Further details of a packaging and inspection system can be found in U.S. patent application Ser. Nos. 10/023,302, 10/023,395, and 10/023,396, filed on Dec. 20, 2001, and previously incorporated by reference into the present application.

Figure 2:
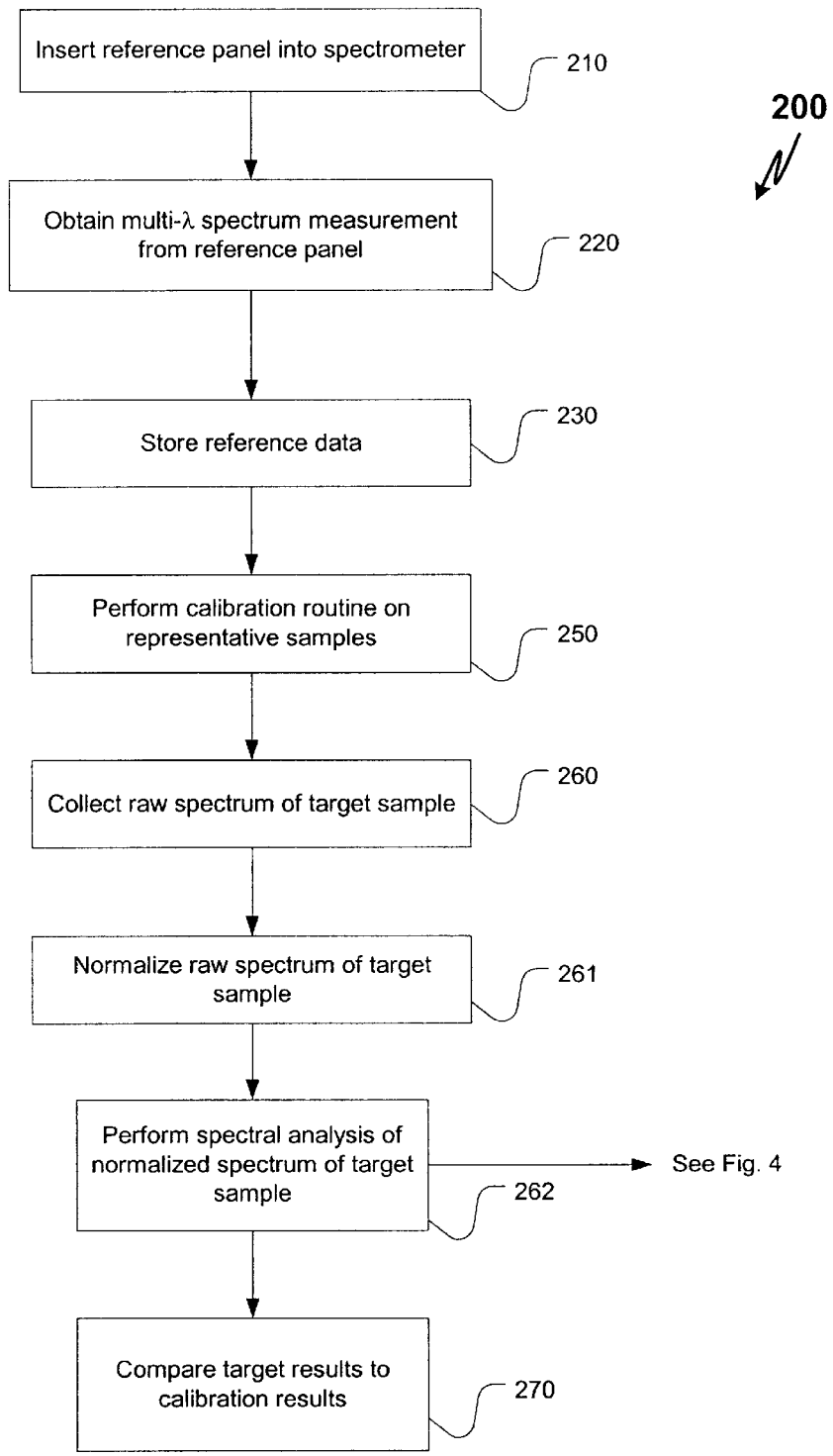
FIG. 2 is a flow chart illustrating a known method for calibrating a spectrometer and analyzing a sample.

Prior to beginning an inspection run utilizing a spectrographic inspection system such as the system 100 described in FIG. 1, the spectrometer system must be calibrated for the material being inspected and must be normalized to a known sample. FIG. 2 shows a known method 200 of performing such a calibration. First, at step 210 a stable reference panel is inserted into the spectrometer's field of view. Typically, a panel with near 100% reflectance is used for this purpose. A multi-wavelength spectrum measurement is then obtained from the reference panel at step 220. Next, this multi-wavelength reference spectrum measurement is stored at step 230. At step 250 a calibration routine is run on the spectrometer system in order to calibrate the spectrometer to the particular type of sample being measured and the specific material property being measured. Typically a range of samples are run through the spectrometer in order to get representative calibration readings. Details of a typical calibration routine are described in conjunction with FIG. 4. However, several additional known calibration routines are also commonly used. Chapter 10 of the *Handbook of Near-Infrared Analysis* by Donald A. Burns and Emil W. Ciurczak (1992), the details of which are hereby incorporated by reference, describes some of these known calibration methods and routines.

After calibrating the spectrometer, a spectrum is collected from the target sample (i.e. a sample that is desired to be measured and tested) at step 260, the raw target spectrum is normalized using the previously stored reference spectrum at step 261, and spectral analysis is performed on a target sample at step 262. The results of this spectral analysis are compared at step 270 to the calibration data previously obtained.

Figure 3:
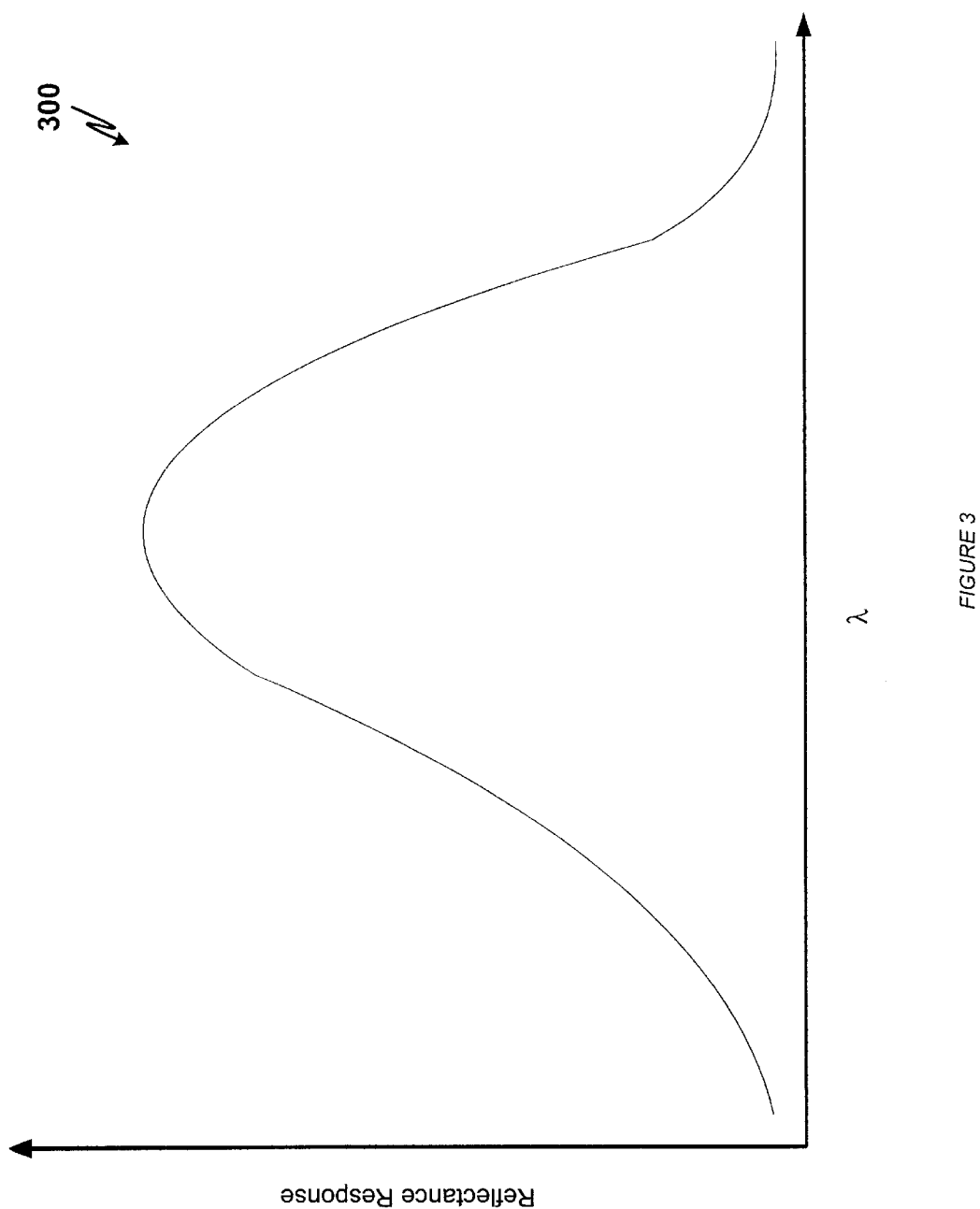
FIG. 3 is a flow chart illustrating a known calibration routine for an NIR spectroscopy system.

The reference panel, preferably having near 100% reflectance, is used to normalize the response of the spectrometer system. FIG. 3 shows a typical response distribution curve 300 of a near 100% reflectance reference panel used for this purpose.

Figure 4:
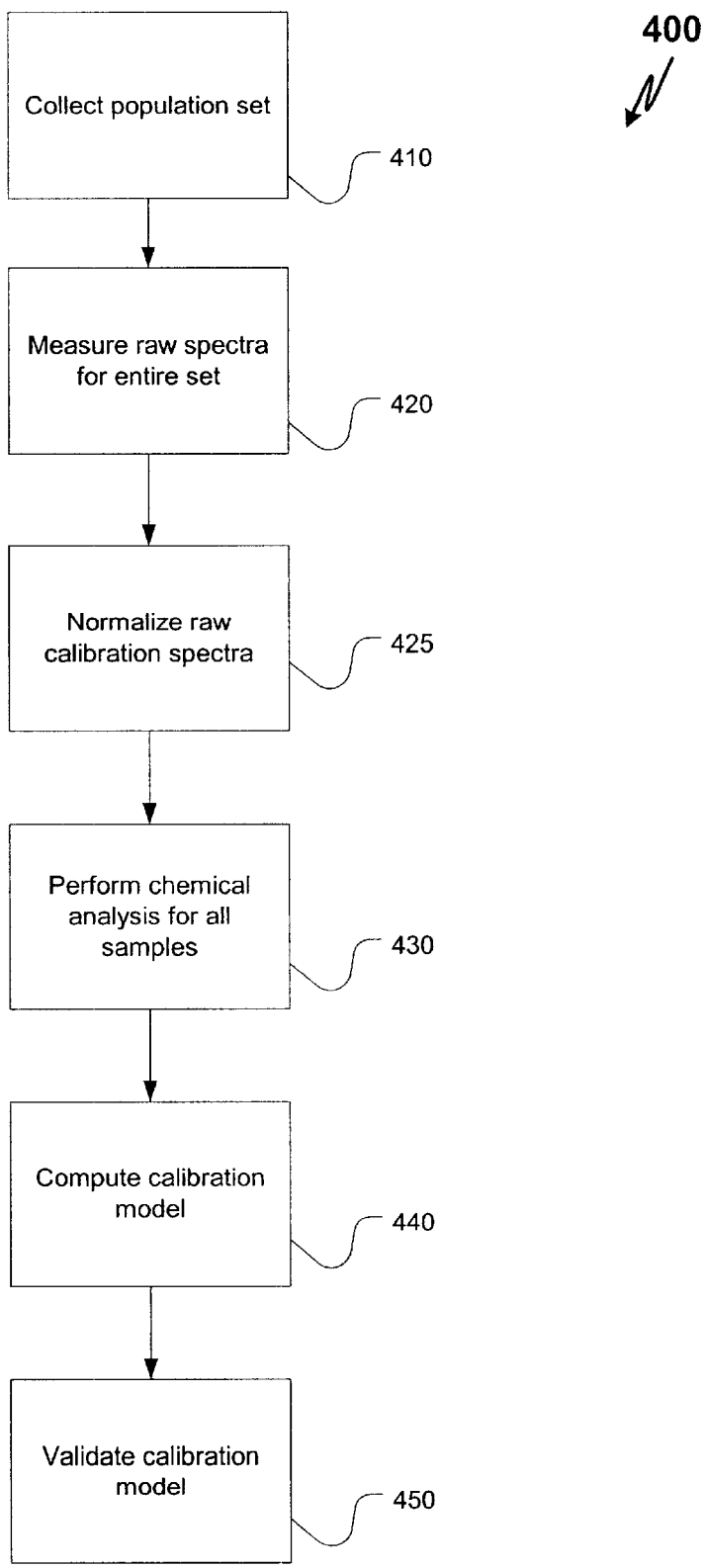
FIG. 4 is a wavelength response graph of a near 100% reflectance reference panel.

FIG. 4 shows a typical calibration routine 400 that is utilized in known systems to "train" the spectrometer to accurately respond to the item being analyzed as well as the specific material property being investigated. First, a population set is collected at step 410 and the raw spectra are measured for the entire population set at step 420. At step 425, each raw spectrum is normalized by dividing the raw spectrum by the reference panel spectrum previously stored. All subsequent calculations are performed on these normalized spectra. A chemical analysis is performed on each of the samples in the population set at step 430 and a calibration model is computed at step 440 using any one of several applicable mathematical models. Finally, the calibration model is validated at step 450.

The requirements of normalizing the spectrometer to a reference panel and performing a separate calibration routine for the spectrometer typically must be completed for each property of each item set being inspected, resulting in a time consuming and expensive procedure. System down time is extended with each inspection property change and several additional levels of error are introduced by the requirement of each of the steps associated with the process of FIGS. 2 and 4.

Figure 5:
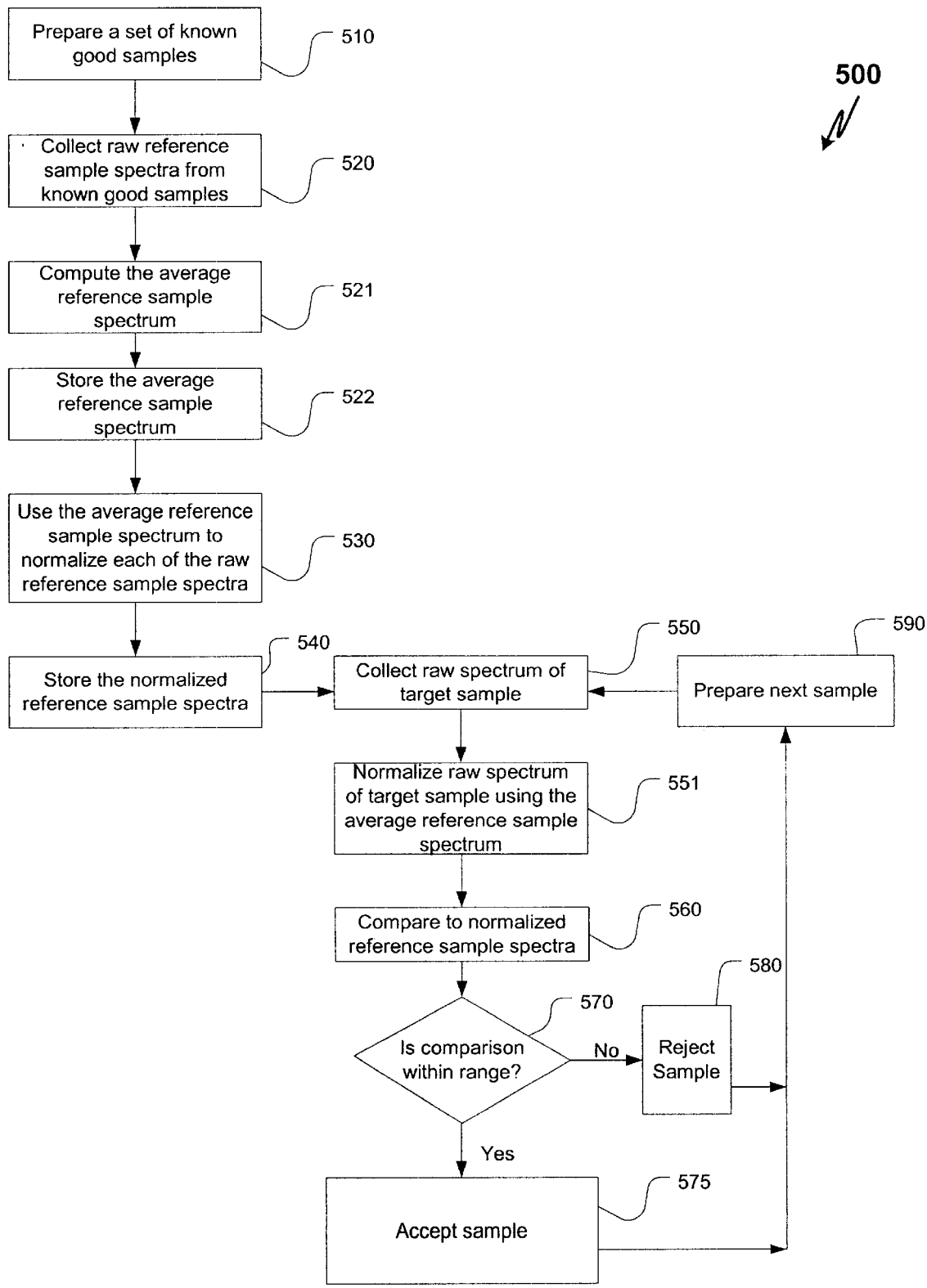
FIG. 5 is a flow chart illustrating a method in accordance with an embodiment of the present invention.
Figure 6:
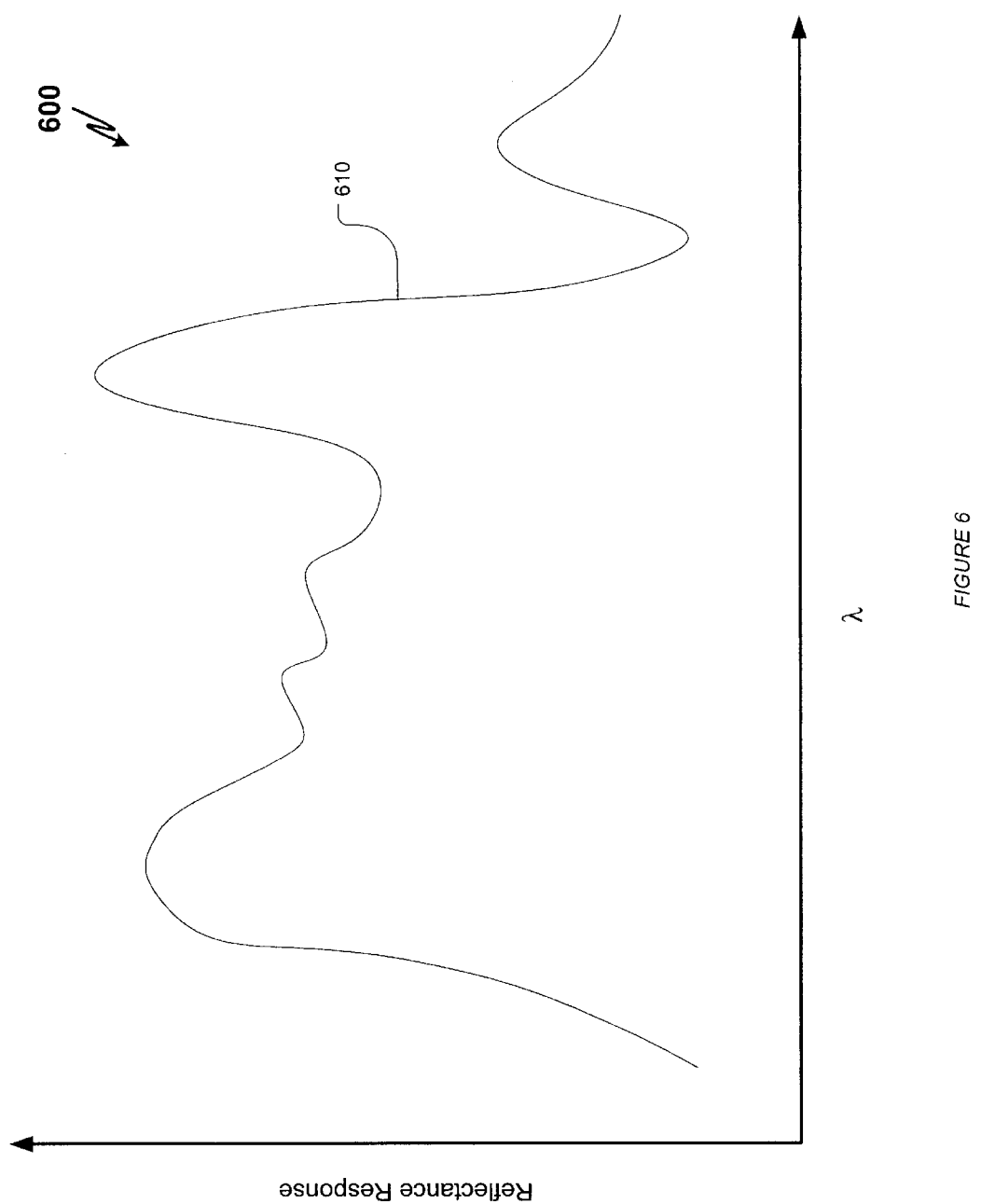
FIG. 6 is a representative wavelength response graph of a known item sample.

FIG. 5 shows an inspection process 500 in accordance with an embodiment of the present invention. A known good and conforming set of samples is prepared at 510. The known sample set is, for example, thirty packages of tablets that have been previously examined or otherwise analyzed and are shown to conform to the material properties of an acceptable level. For instance, if a particular inspection process is being run to test for a proper level of active ingredient, the package of tablets prepared at 510 has been verified to conform to the proper level of active ingredient. Alternatively, the conformance of the packages may be verified after the data collection. At 520, each of the packages containing the known samples are run through the spectrometer and a multi-wavelength spectra measurement is obtained for each package of known samples. The measurements are referred to as the reference sample spectra. The reference sample spectral measurements are averaged at 521 and this averaged data is stored, for instance in a processor or other type of data storage device, at 522. At 530, each of the raw reference sample spectra collected at 520 are normalized by dividing by the average reference sample spectrum previously stored at 522. These normalized reference sample spectra are stored at 540.

A raw spectral measurement is then obtained on a target sample at 550. The target sample is preferably a real-time measurement of an unknown item or group of items that a user would want to inspect. For example, during a normal packaging and inspection run, blister packages filled with tablets that have not yet been examined for conformance with any particular properties would be run through the inspection process, where each of the packages constituting a target sample. The spectrum collected from the target sample is then normalized at 551 by dividing by the average reference sample measurement. The normalized spectrum from the target sample is then compared at 560 to the normalized reference sample spectra. At 570 a determination is made whether the target spectra is within acceptable limits of the reference data. If the package is conforming, the package is accepted at 575 and another sample is prepared at 590. The inspection process then repeats. If the package is not conforming, then the target sample is rejected at 580 and another sample is prepared at 590. The inspection process repeats until all targets have been inspected. FIG. 7 shows the reflectance response curve 600 of a known sample.

By utilizing a set of known good samples of the product being inspected to both serve as a reference sample for normalizing the spectral response of the spectrometer and for comparison to the spectra response curve of an unknown sample, the calibration step is eliminated as well as a potential large source of error. Additionally, by utilizing an inspection method in accordance with an embodiment of the present invention, there is no need to load the packaging and inspection equipment with a white-panel reference sample at the beginning of an inspection run and it is possible to develop calibrations for specific material properties (e.g. moisture, density) that are applicable to a range of material compositions. In known inspection systems, these calibrations must be developed separately for each material composition.

Although the present invention had been described and illustrated in the above description and drawings, it is understood that this description is by example only and that numerous changes and modifications can be made by those skilled in the art without departing from the true spirit and scope of the invention. The invention, therefore, is not to be restricted, except by the following claims and their equivalents.

What is claimed is:

1. A method of calibrating a spectrographic inspection system, comprising:
   providing a plurality of packages, each of the plurality of packages containing a group of items, wherein each of the groups of items has a known composition;
   measuring the reflectance value of each of the groups of items and thereby obtaining a reference reflectance value set;
   normalizing the reference reflectance value set and thereby creating a normalized reference reflectance value set; and
   storing the normalized reference reflectance value set.

2. The method of claim 1, further comprising defining an acceptable range of target reflectance values based on the normalized reference reflectance value set.

3. The method of claim 2, further comprising using the acceptable range of target reflectance values to evaluate a package containing a group of items, wherein the group of items has an unknown composition.

4. The method of claim 1, further comprising associating the normalized reference reflectance value set with a specific material property.

5. The method of claim 4, wherein the specific material property is chosen from the group comprising moisture content, density, color, chemical composition, coating, and thickness.

6. The method of claim 1, wherein the reference reflectance value sets comprises data corresponding to a range of wavelengths.

7. The method of claim 6, wherein the range of spectra is approximately 350 nm to 2500 nm.

8. The method of claim 1, wherein each of the groups of items are arranged in an array of tablet wells.

9. The method of claim 1, wherein the plurality of packages are blister-packs.

10. A method of analyzing a package of items, comprising:
   providing a first package containing a first group of items, wherein the first group of items has a known composition;
   measuring the reflectance value of the first group of items, thereby obtaining a reference reflectance value;
   normalizing the reference reflectance value and thereby creating a normalized reference reflectance value;
   storing the normalized reference reflectance value;
   providing a second package containing a second group of items, wherein the second group of items has an unknown composition;
   measuring the reflectance value of the second group of items to obtain a target reflectance value;
   normalizing the target reflectance value and thereby creating a normalized target reflectance value;
   comparing the normalized target reflectance value with the normalized reference reflectance value; and
   determining whether the normalized target reflectance value conforms with the normalized reference reflectance value.

11. The method of claim 10, wherein determining whether the normalized target reflectance value conforms with the normalized reference reflectance value comprises:
   calculating the minimum difference between the normalized reference reflectance value and the normalized target reflectance value; and
   determining if the computed minimum distance is within a pre-determined acceptable range.

12. The method of claim 10, wherein determining whether the normalized target reflectance value conforms with the normalized reference reflectance value comprises calculating whether the normalized target reflectance value is within a pre-determined number of standard deviations of the mean of the normalized reference reflectance value.

13. An inspection system, comprising:
   an inspection station adapted to obtain reflectance data corresponding to a first package and adapted to gather reflectance data corresponding to a second package; and
   a processor communicatively coupled with the inspection station and adapted to normalize the reflectance data obtained by the inspection station, thereby creating normalized reflectance data, wherein the processor is further adapted to compare the reflectance data corresponding to the first package with the normalized reflectance data corresponding to the second package.

14. The system of claim 13, further comprising a data storage device communicatively coupled to the processor and adapted to retain the normalized reflectance data for later use.

15. The system of claim 13, wherein the first package is a reference package and the second package is a target package.

16. The system of claim 13, wherein the first package contains a plurality of items having a known composition.

17. The system of claim 13, wherein the second packages contains a plurality of items having an unknown composition.

18. The system of claim 13, wherein the inspection station comprises a sample probe adapted to receive light energy and pass the light energy to the inspection station.

19. The system of claim 13, wherein the inspection station includes a spectrometer.

20. The system of claim 13, wherein the inspection station is adapted to receive a sample probe.

21. The system of claim 13, wherein the inspection station is integrated into a packaging system.

22. A spectrographic inspection system, comprising:
   means for obtaining a first reflectance value corresponding to a first group of items having a known composition;
   means for obtaining a second reflectance value corresponding to a second group of items having an unknown composition;
   means for normalizing the first reflectance value;
   means for storing the normalized first reflectance value;
   means for comparing the normalized first reflectance value with the second reflectance value; and
   means for determining whether the second reflectance value conforms with the normalized first reflectance value.

* * * * *